US00PP22988P3

(12) United States Plant Patent
Radler

(10) Patent No.: US PP22,988 P3
(45) Date of Patent: Aug. 28, 2012

(54) SHRUB ROSE PLANT NAMED 'RADFRAGWHITE'

(50) Latin Name: *Rosa hybrida*
Varietal Denomination: Radfragwhite

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 21 days.

(21) Appl. No.: 12/805,912

(22) Filed: Aug. 24, 2010

(65) Prior Publication Data

US 2012/0054925 P1 Mar. 1, 2012

(51) Int. Cl.
*A01H 5/00* (2006.01)

(52) U.S. Cl. ..... Plt./102

(58) Field of Classification Search ..... Plt./103, Plt./102, 130, 132, 133, 143, 144
See application file for complete search history.

*Primary Examiner* — June Hwu

(74) *Attorney, Agent, or Firm* — Buchanan Ingersoll & Rooney PC

(57) ABSTRACT

A new and distinct shrub rose plant is provided that abundantly and substantially continuously forms attractive double blossoms that are white with a pink hue at the edges of the petals. The plant exhibits vigorous vegetation and a bushy and upright growth habit. The ornamental foliage is dark green with a matte finish. The blossoms are very fragrant. The plant is well suited for growing as attractive ornamentation in parks and gardens.

1 Drawing Sheet

Botanical/commercial classification: *Rosa hybrida*/Shrub Rose Plant.

Varietal denomination: cv. Radfragwhite.

SUMMARY OF THE INVENTION

The new variety of *Rosa hybrida* shrub rose plant of the present invention was created during June 2002 at Greenfield, Wis., U.S.A., by artificial pollination wherein two parents were crossed which previously had been studied in the hope that they would contribute the desired characteristics. The female parent (i.e., the seed parent) was the 'Radbrite' variety (U.S. Plant Pat. No. 17,391). The male parent (i.e., the pollen parent) of the new variety was the 'Radell' variety (non-patented in the United States). The parentage of the new variety can be summarized as follows:

'Radbrite'×'Radell'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive very fragrant double white blossoms with a pink hue at the edges of the petals,
(b) exhibits a bushy and upright growth habit,
(c) forms vigorous vegetation,
(d) forms attractive ornamental dark green foliage having a matte finish,
(e) exhibits good resistance to disease, and
(f) is well suited for providing attractive ornamentation in the landscape.

A new rose variety is provided having attractive fragrant white blossoms combined with substantially continuous blooming and good disease resistance.

The new variety well meets the needs of the horticultural industry. It can be grown to advantage as ornamentation in parks, gardens, public areas, and in residential settings. Accordingly, the new variety is particularly well suited for growing in the landscape. The new variety also can be readily distinguished from its 'Radell' parent in a number of respects. 'Radell' commonly forms larger clear medium pink blooms that are borne mostly one per stem. The leaflets of 'Radell' tend to be more pointed while those of the new variety tend to be smaller and more rounded. The new growth of 'Radell' is a noticeably colorful reddish-burgundy unlike that of the new variety. The fragrance of 'Radell' tends to be spicy unlike the citrus fragrance of the new variety. Also, the growth habit of the new variety tends to be somewhat more upright than that of the 'Radell' variety. The white blossoms contrast nicely with the dark green foliage having a matte finish.

The new variety of the present invention can be readily distinguished from its ancestors as well as from previously available varieties such as the 'Radwhite' variety (U.S. Plant Pat. No. 20,273). More specifically, the blossoms of the 'Radbrite' variety are pink with a yellow eye and a dissimilar climbing growth habit is displayed by such variety. The blossoms of the 'Radwhite' variety are initially light yellow and turn to white when mature.

The characteristics of the new variety have been found at Waso, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radfragwhite', and will be marketed in the United States under the MILWAUKEE'S CALATRAVA trademark.

BRIEF DESCRIPTION OF THE PHOTOGRAPH

The accompanying photograph shows, as nearly true as it is reasonably possible to make the same in a color illustration of this character, typical blossoms of the new variety in various stages of development. The illustrated rose plant of the new variety was approximately four years of age and was observed during July 2009 while growing outdoors near West Grove, Pa., U.S.A. The red hue at the edges of the petals is readily apparent on the blossoms present at the center and left.

DETAILED DESCRIPTION

The chart used in the identification of colors is that of The Royal Horticultural Society (R.H.S. Colour Chart-1995 or equivalent), London, England. The description is based on the observation of two-year-old specimens of the new variety during July while growing outdoors in containers near West Grove, Pa., U.S.A.

Class: Landscape Shrub.

Plant:

*Height*.—Approximately 3.5 feet on average at the end of the growing season.

*Width*.—Approximately 3.5 feet on average at the end of one growing season.

*Habit*.—Upright and bushy.

Branches:

*Color*.—Young stems: near Yellow-Green Group 144B. Adult wood: Green Group 137B.

*Surface texture*.—Young stems: smooth. Adult stems: somewhat rough.

*Thorns*.—Size: approximately 8 to 10 mm in length on average, and commonly near Yellow-Green Group 144B infused with Greyed-Purple Group 183C in coloration.

Leaves:

*Length*.—Approximately 10.4 cm on average for a five-leaflet leaf.

*Width*.—Approximately 8 cm on average for a five-leaflet leaf.

*Leaflets*.—Number: 3, 5, and 7. Length: approximately 4.5 cm on average for a terminal leaflet, and approximately 2.8 cm on average for a lower leaflet. Width: approximately 2.7 cm on average for a terminal leaflet, and approximately 2 cm on average for a lower leaflet. Shape: ovate. Margins: biserrate. Texture: smooth on the upper surface, and thorny along the midrib and otherwise smooth on the under surface. Overall appearance: attractive dark green with a matte finish. Color (young foliage): Upper surface: commonly Yellow-Green Group 144A. Under surface: commonly Green Group 138B. Color (adult foliage): Upper surface: commonly Green Group 137A. Under surface: commonly Green Group 137D.

Inflorescence:

*Bearing*.—Typically one blossom per stem.

*Number of flowers*.—Commonly approximately 23 blooms on average per plant when observed.

*Peduncle*.—Near Greyed-Purple Group 186A in coloration, commonly approximately 5 cm in length, smooth in texture, and commonly covered with flexible thorns having a length of approximately 1 mm.

*Sepals*.—Upper surface: commonly near Yellow-Green Group 144B at the base and near Green Group 137A at the apex. Under surface: smooth and near Yellow-Green Group 144B at the base and near Yellow-Green Group 147B at the apex. Size: commonly approximately 3.5 cm in length on average, and approximately 1.5 cm in width at the widest point. Number: five.

*Buds*.—Shape: ovoid. Length: approximately 1.5 cm on average as the calyx breaks. Diameter: approximately 1.3 cm on average as the calyx breaks. Color: Red Group 52D.

*Flower*.—Form: double. Shape: cuplike and double. Diameter: approximately 6 cm on average when fully open. Color (when opening begins): Upper surface: near White Group 155B with some Red Group 56D at the edges. Under surface: near White Group 155A with some Red Group 56B at the edges. Color (at end of blooming): Upper surface: near Yellow-White Group 158B. Under surface: some near Red Group 56D. Fragrance: very fragrant and reminiscent of fresh citrus. Petal number: commonly approximately 21 on average. Petal length: approximately 3.2 cm on average. Pedal width: approximately 3.6 cm on average. Overall petal shape: broadly obcordate. Petal margin: entire with a tendency to reflex. Petal apex: broadly obcordate. Apex shape: broadly obcordate. Base shape: broadly cuneate. Petal drop: good, the petals commonly drop cleanly at full maturity. Stamen: approximately 73 on average, and regularly arranged about the pistils. Anthers: near Orange Group 26A in coloration. Filaments: approximately 6 mm in length, and near Yellow Group 6D in coloration. Pollen: light-orange in coloration. Pistils: separate and free, and approximately 30 in number on average. Styles: approximately 5 mm in size and Red-Purple Group 63C in coloration. Stigmas: less than 1 mm in size and Yellow Group 5D in coloration. Receptacle: substantially spherical, approximately 7 mm in diameter, smooth surface texture, and near Green-White Group 157A in coloration.

Development:

*Vegetation*.—Vigorous and strong.

*Blossoming*.—Abundant and substantially continuous during the growing season.

*Resistance to insects*.—Has proven to be resistant to leafhoppers and midge during observations to date.

*Tolerance to disease*.—Good with respect to Blackspot, Mildew, and Rust during observations to date.

*Hardiness*.—During observations to date the plant has proven to be hardy to U.S.D.A. Hardiness Zone No. 5.

*Formation of hips/seeds*.—Sparse, and none available for inspection.

I claim:

1. A new and distinct shrub rose plant characterized by the following combination of characteristics:

(a) abundantly and substantially continuously forms attractive very fragrant double white blossoms with a pink hue at the edges of the petals, (b) exhibits a bushy and upright growth habit, (c) forms vigorous vegetation, (d) forms attractive ornamental dark green foliage having a matte finish, (e) exhibits good resistance to disease, and (f) is well suited for providing attractive ornamentation in the landscape;

substantially as herein shown and described.

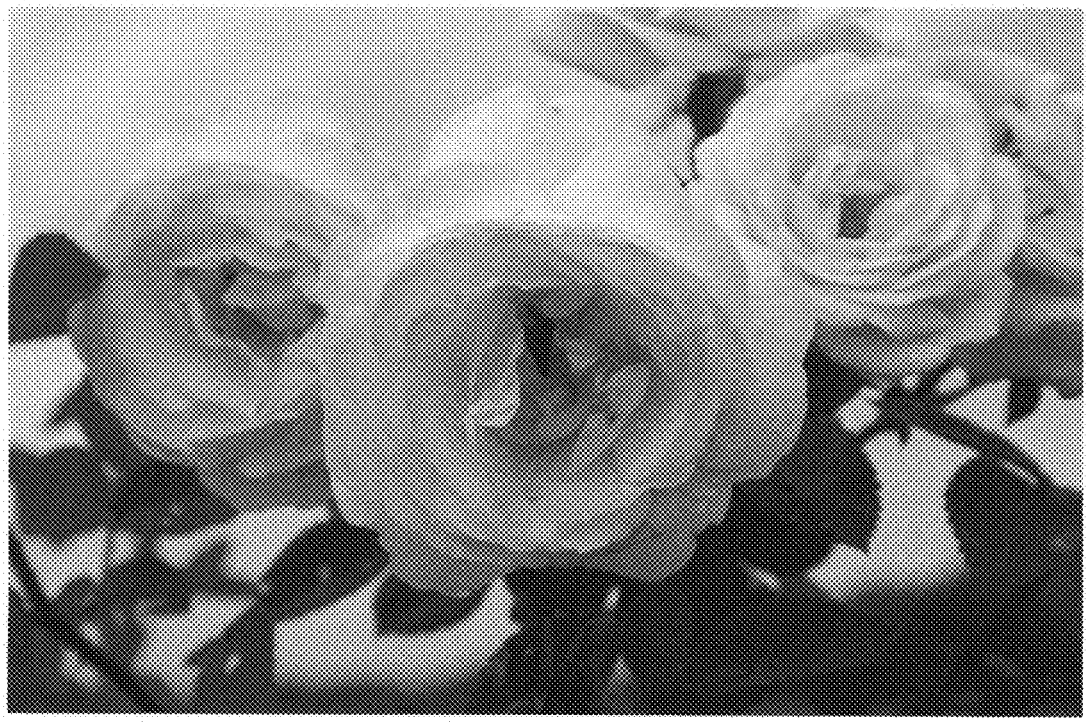

* * * * *